(12) United States Patent
Goldstein et al.

(10) Patent No.: US 8,062,848 B2
(45) Date of Patent: *Nov. 22, 2011

(54) NUCLEIC ACID-FREE THERMOSTABLE ENZYMES AND METHODS OF PRODUCTION THEREOF

(75) Inventors: Adam Goldstein, New Market, MD (US); A. John Hughes, Jr., Temecula, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/433,869

(22) Filed: Apr. 30, 2009

(65) Prior Publication Data

US 2009/0215126 A1    Aug. 27, 2009

Related U.S. Application Data

(63) Continuation of application No. 11/135,535, filed on May 24, 2005, now abandoned, which is a continuation of application No. 10/342,237, filed on Jan. 15, 2003, now Pat. No. 6,905,858, which is a continuation of application No. 09/866,816, filed on May 30, 2001, now Pat. No. 6,531,301, which is a continuation of application No. 09/229,967, filed on Jan. 14, 1999, now Pat. No. 6,245,533, which is a continuation of application No. 08/778,082, filed on Jan. 2, 1997, now Pat. No. 5,861,295.

(51) Int. Cl.
  *C12Q 1/68*    (2006.01)
  *C12P 19/34*   (2006.01)
(52) U.S. Cl. ............ 435/6.11; 435/6.12; 435/91.1; 435/91.2
(58) Field of Classification Search ............ 435/6, 91.1, 435/91.2
See application file for complete search history.

(56) References Cited

U.S. PATENT DOCUMENTS

| | | |
|---|---|---|
| 4,659,667 A | 4/1987 | Brewer et al. |
| 4,683,195 A | 7/1987 | Mullis et al. |
| 4,683,202 A | 7/1987 | Mullis |
| 4,889,818 A | 12/1989 | Gelfand et al. |
| 5,079,352 A | 1/1992 | Gelfand et al. |
| 5,310,652 A | 5/1994 | Gelfand et al. |
| 5,322,770 A | 6/1994 | Gelfand |
| 5,322,785 A | 6/1994 | Comb et al. |
| 5,352,600 A | 10/1994 | Gelfand et al. |
| 5,374,553 A | 12/1994 | Gelfand et al. |
| 5,405,774 A | 4/1995 | Abramson et al. |
| 5,407,800 A | 4/1995 | Gelfand et al. |
| 5,417,862 A | 5/1995 | Bergemann et al. |
| 5,418,149 A | 5/1995 | Gelfand et al. |
| 5,420,029 A | 5/1995 | Gelfand et al. |
| 5,455,170 A | 10/1995 | Abramson et al. |
| 5,466,591 A | 11/1995 | Abramson et al. |
| 5,516,292 A | 5/1996 | Steinman |
| 5,532,145 A | 7/1996 | Tessman et al. |
| 5,561,058 A | 10/1996 | Gelfand et al. |
| 5,618,703 A | 4/1997 | Gelfand et al. |
| 5,618,711 A | 4/1997 | Gelfand et al. |
| 5,624,833 A | 4/1997 | Gelfand et al. |
| 5,641,864 A | 6/1997 | Gelfand |
| 5,674,738 A | 10/1997 | Abramson et al. |
| 5,693,517 A | 12/1997 | Gelfand et al. |
| 5,789,224 A | 8/1998 | Gelfand et al. |
| 5,795,762 A | 8/1998 | Abramson et al. |
| 5,861,295 A | 1/1999 | Goldstein et al. |
| 5,968,799 A | 10/1999 | Gelfand et al. |
| 6,127,155 A | 10/2000 | Gelfand et al. |
| 6,245,533 B1 | 6/2001 | Goldstein et al. |
| 6,531,301 B2 | 3/2003 | Goldstein et al. |
| 6,630,333 B1 | 10/2003 | Hughes, Jr. |
| 6,905,858 B2 | 6/2005 | Goldstein et al. |
| 6,127,155 C1 | 7/2007 | Gelfand et al. |

FOREIGN PATENT DOCUMENTS

| | | |
|---|---|---|
| EP | 0329822 | 8/1989 |
| EP | 0534858 | 3/1993 |
| EP | 0684315 | 11/1995 |
| WO | WO-98/47912 | 10/1998 |

OTHER PUBLICATIONS

U.S. Appl. No. 10/342,237, Notice of Allowance Mailed Feb. 10, 2005.
U.S. Appl. No. 10/342,237, Office Action Mailed Oct. 20, 2004.
U.S. Appl. No. 10/342,237, Office Action Mailed Apr. 2, 2004.
U.S. Appl. No. 10/342,237, Response to Office Action Mailed Oct. 20, 2004, filed on Jan. 10, 2005.
U.S. Appl. No. 10/342,237, Response to Office Action Mailed Apr. 20, 2004, filed on Jul. 2, 2004.
U.S. Appl. No. 11/135,535, Notice of Allowance mailed on Dec. 5, 2006.
U.S. Appl. No. 11/135,535, Office Action mailed on Jan. 23, 2008.
U.S. Appl. No. 11/135,535, Office Action mailed on Feb. 2, 2007.
U.S. Appl. No. 11/135,535, Office Action mailed on Jul. 12, 2006.
U.S. Appl. No. 11/135,535, Office Action mailed on Aug. 17, 2007.
U.S. Appl. No. 11/135,535, Office Action mailed on Oct. 30, 2008.
U.S. Appl. No. 11/135,535, Office Action mailed on Nov. 14, 2005.
U.S. Appl. No. 11/135,535, Response to Jan. 23, 2008 Office Action, filed on Jul. 23, 2008.
U.S. Appl. No. 11/135,535, Response to Feb. 2, 2007 Office Action, filed on Jun. 4, 2007.
U.S. Appl. No. 11/135,535, Response to Jul. 12, 2006 Office Action, filed on Nov. 13, 2006.
U.S. Appl. No. 11/135,535, Response to Aug. 17, 2007 Office Action, filed on Dec. 17, 2007.
U.S. Appl. No. 11/135,535, Response to Nov. 14, 2005 Office Action, filed on May 11, 2006.
Amos, H., et al., "Protein Synthesis in Sonically Damaged *Escherichia coli*," *J. Bacteriol.* 94:232-240, American Society for Microbiology (1967).

(Continued)

*Primary Examiner* — Kenneth R. Horlick (57) ABSTRACT

The present invention provides thermostable enzymes, such as DNA polymerases and restriction endonucleases, that are substantially free from contamination with nucleic acids. The invention also provides methods for the production of these enzymes, and kits comprising these enzymes which may be used in amplifying or sequencing nucleic acid molecules, including through use of the polymerase chain reaction (PCR).

18 Claims, 2 Drawing Sheets

OTHER PUBLICATIONS

Brock, T.D. And Freeze, H., "*Thermus aquaticus* gen. n. and sp. n., a Non-sporulating Extreme Thermophile," *J. Bact.* 98:289-297, American Society for Microbiology (1969).

Caetano-Anolles, G. et al., "DNA Amplification Fingerprinting Using Very Short Arbitrary Oligonucleotide Primers," *Bio/Technol.* 9:553-557, Nature Publishing Co. (1991).

Cull, M., and McHenry, C.S., "Preparation of Extracts from Prokaryotes," *Meth. Enzymol.*182:147-153, Academic Press, Inc. (1990).

Elie, c., et al., "A DNA polymerase from a thermoacidophilic archaebacterium: evolutionary and technological interests," *Biochem. Biophys. Acta* 951:261-267, Elsevier (1988).

Felix, H., "Permeabilized Cells," *Anal. Biochem.* 120:211-234, Academic Press, Inc. (1982).

Gerard, G.P., "Synthesis of High Specific Activity cDNA," *Focus* 10:1:12-13, Invitrogen (1988).

Gubler, U. and Hoffman, B.J., "A simple and very efficient method for generating cDNA libraries," *Gene* 25:263-269, Elsevier Science Publishers (1983).

Harrell, R.A. II, and Hart, R.P., "Rapid Preparation of *Thermus flavus* DNA Polymerase," *PCR Meth. Appl.* 3:372-375, Cold Spring Harbor Laboratory Press, (1994).

Hettwer, D., and Wang, H., "Protein Release from *Escherichia coli* Cells Permeabilized with Guanidine-HC1 and Triton X100," *Biotechnol. Bioeng.* 33:886-895, New York: John Wiley & Sons, Inc, (1989).

Houdebine, L.-M., "Synthesis of DNA complementary to the mRNAs for milk proteins by *E.coli* DNA polymerase I.," *Nucl. Acids Res.* 3:615-630, Oxford University Press (1976).

Hughes, A.J.,Jr. et al., "Expression, Purification, and Characterization of an *Escherichia coli* Phage TS DNA Polymerase 3'-5' Exonuclease Mutant," *J. Cell Biochem.* 16B:84, Abstract No. F 538, Wiley-Liss, Inc. (1992).

Hughes, M.S., et al., "Identification and Elimination ofDNA Sequences in Taq DNA Polymerase," *J. Clin. Microbiol.* 32:2007-2008, American Society of Microbiology (1994).

Kim, Y. et al., "Crystal Structure of *Thermus acquatics* DNA Polymerase", *Nature* vol. 376:612-616 (1995).

Kim, Y. et al., "Structure of TAQ DNA Polymerase", *Protein Data Bank* www.rcsb.org/pdb/explore.do?structureID=1Taq (Jul. 22, 2008).

Kimmel, A.R. and Berger, S.L., "Preparation of cDNA and the Generation of cDNA Libraries: Overview," *Meths. Enzymol.* 152:307-317, Academic Press, Inc. (1987).

Laurent, S.J., and Vannier, P.S., "Permeabilization of *B. subtilis* cells to macromolecules," *Biochimie* 59:747-750, Elsevier (1977).

Lazzarini, R.A., and Johnson, L.D., "Regulation of Ribosomal RNA Synthesis in Cold-shocked *E. coli*," *Nature New Biology* 243:17-20, Macmillan Journals Limited (1973).

Maniatis, T. et al., "Synthesis of cDNA," in *Molecular Cloning. A Laboratory Manual*, Maniatis, T. et al., eds., Cold Spring Harbor Laboratory Press, Cold Spring Harbor, NY pp. 213-231 (1982).

McCoy, J., and LaVallie, E., "*E. coli* Lysis Using a French Pressure Cell," in *Current Protocols in Molecular Biology*, Ausubel, P.M., et al., eds. pp. 16.8.6-16.8.14, New York: John Wiley & Sons (1995).

McHenry, c., and Kornberg, A., "DNA Polymerase III Holoenzyme of *Escherichia coli*: Purification and Resolution into Subunits," *J. Biol. Chern.* 252:6478-6484, The American Society of Biological Chemists, Inc. (1977).

Meyer, W., et al., "Purification, Cloning, and Sequencing of Archaebacterial Pyrophosphatase from the Extreme Thermoacidophile *Sul/olobus acidocaldarius*," *Arch. Biochem. Biophys.* 319:149-156, Academic Press, Inc. (1995).

Mowshowitz, D.B., "Permeabilization of Yeast for Enzyme Assays: An Extremely Simple Method for Small Samples," *Anal. Biochem.* 70:94-99, Academic Press, Inc. (1976).

Oshima, T., and Imahori, K., "Description of *Thermus thermophilus* (Yoshida and Oshima) comb. nov., a Nonsporulating Thermophilic Bacterium from a Japanese Thermal Spa," *Int. J. Syst. Bacteriol.* 24:102-112, International Association of Microbiological Societies (1974).

Palm, P., et al., "The DNA-dependent RNA-polymerase of *Thermotoga maritima*; characterisation of the enzyme and the DNA-sequence of the genes for the large subunits," *Nucl. Acids Res.* 21:4904-4908, Oxford University Press (1993).

Park, J .H., et al., "Purification and characterization of *Thermus caldophilus* GK24 DNApolymerase," *Eur. J. Biochem.* 214:135-140, Federation of European Biochemical Societies (1993).

Putnam, S.L., and Koch, A.L., "Complications in the Simplest Cellular Enzyme Assay: Lysis of *Escherichia coli* for the Assay of β-Galactosidase," *Anal. Biochem.* 63:350-360, Academic Press, Inc. (1975).

Rand, K.H., and Houck, H., "*Taq* polymerase contains bacterial DNA of unknown origin," *Mol. Cell. Probes* 4:445-450, Academic Press Limited (1990).

Reddy, K.J., and Gilman, M., "Preparation of Bacterial RNA," in *Current Protocols in Molecular Biology*, Ausubel, P.M., et al., eds. pp. 4.4.1-4.4.7, New York: John Wiley & Sons (1993).

Roberts, J.D., and Lieberman, M.W., "Deoxyribonucleic Acid Repair Synthesis in Permeable Human Fibroblasts Exposed to Ultraviolet Radiation and *N-Acetoxy-2-*(acetylamino) fluorene," *Biochemistry* 18:4499-4505, American Chemical Society (1979).

Roth, M.J. et al., "Purification and Characterization of Murine Retroviral Reverse Transcriptase Expressed in *Escherichia coli*," *J. Biol. Chern.* 260:9326-9335, The American Society of Biological Chemists, Inc. (1985).

Rupp, Bernhard et al., "Predictive Models for Protein Crystallization", *Methods* 34:390-407 (2004).

Sambrook, J., et al., "Cell Lysis," in *Molecular Cloning: A Laboratory Manual, 2nd* Ed., Cold Spring Harbor, NY, Cold Spring Harbor Laboratory Press, pp. 17.38 (1989).

Sambrook, J. et al., "Harvesting and Lysis of the Bacteria," in *Molecular Cloning: A Laboratory Manual, 2nd* Ed., Sambrook, J., et al., eds., Cold Spring Harbor Laboratory Press, Cold Spring Harbor, NY, pp. 1.22-1.23 (1989).

Sambrook, J. et al., "Preparation of Protoplasts," in *Molecular Cloning: A Laboratory Manual, 2nd* Ed., Sambrook, J., et al., eds., Cold Spring Harbor Laboratory Press, Cold Spring Harbor, NY, pp. 16.49 (1989).

Schupp, J.M., et al., "Rapid Bacterial Permeabilization Reagent Useful for Enzyme Assays," *Bio Techniques* 19:18-20, Eaton Publishing Co. (1995).

Shinomiya, T., et al., "A New Aspect of a Restriction Endonuclease *Tth*lII I. It Has a Degenerated Specificity (*Tth*lII 1*)," *J. Biochem.* 92:1823-1832, The Japanese Biochemical Society (1982).

Urs, U. K. et al., "Characterization of Crystals of the Thermostable DNA Polymerase I from *Thremus aquaticus*", *Proteins: Structure, Function, and Genetics* 23 Wiley-Liss, Inc., pp. 111-114 (1995).

NUCLEIC ACID-FREE THERMOSTABLE ENZYMES AND METHODS OF PRODUCTION THEREOF

The present application is a continuation of U.S. patent application Ser. No. 11/135,535 (now abandoned), filed May 24, 2005; which is a continuation of U.S. patent application No. 10/342,237 (now U.S. Pat. No. 6,905,858), filed Jan. 15, 2003; which is a continuation of U.S. patent Application Ser. No. 09/866,816 (now U.S. Pat. No. 6,531,301), filed May 30, 2001; which is a continuation of U.S. patent application Ser. No. 09/229,967 (now U.S. Pat. No. 6,245,533), filed Jan. 14, 1999; which is a continuation of U.S. patent application Ser. No. 08/778,082 (now U.S. Pat. No. 5,861,295), filed Jan. 2, 1997, the contents of which are entirely incorporated herein by reference.

FIELD OF THE INVENTION

The present invention is in the fields of molecular biology and protein chemistry. Specifically, the invention provides compositions comprising thermostable enzymes, particularly thermostable DNA polymerases and restriction endonucleases, that are substantially free from contamination by nucleic acids, and methods for the production of such thermostable enzymes. Compositions comprising the thermostable enzymes of the present invention may be used in a variety of applications, including amplification and sequencing of nucleic acids.

BACKGROUND OF THE INVENTION

A variety of techniques have been traditionally employed to facilitate the preparation of intracellular proteins from microorganisms. Typically, the initial steps in these techniques involve lysis, rupture or permeabilization of the bacterial cells, to disrupt the bacterial cell wall and allow release of the intracellular proteins into the extracellular milieu. Following this release, the desired proteins are purified from the extracts, typically by a series of chromatographic steps:

Several approaches have proven useful in accomplishing the release of intracellular proteins from bacterial cells. Included among these are the use of chemical lysis or permeabilization, physical methods of disruption, or a combination of chemical and physical approaches (reviewed in Felix, H., *Anal. Biochem.* 120:211-234 (1982)).

Chemical methods of disruption of the-bacterial cell wall that have proven useful include treatment of cells with organic solvents such as toluene (Putnam, S. L., and Koch, A. L., *Anal. Biochem.* 63:350-360 (1975); Laurent, S. J., and Vannier, F. S., *Biochimie* 59:747-750 (1977); Felix, H., *Anal. Biochem.* 120:211-234 (1982)), with chaeotropes such as guanidine salts (Hettwer, D., and Wang, H., *Biotechnol. Bioeng.* 33:886-895 (1989)), with antibiotics such as polymyxin B (Schupp, J. M., et al., *BioTechniques* 19:18-20 (1995); Felix, H., *Anal. Biochem.* 120:211-234 (1982)), or with enzymes such as lysozyme or lysostaphin (McHenry, C. S, and Kornberg, A, *J. Biol. Chem.* 252(18):6478-6484 (1977); Cull, M., and McHenry, C. S., *Meth Enzymol.* 182: 147-153 (1990); Hughes, A. J., Jr., et al., *J. Cell. Biochem. Suppl.* 0 16 (*Part B*):84 (1992); Sambrook, J., et al., in: *Molecular Cloning: A Laboratory Manual,* 2nd ed., Cold Spring Harbor, N.Y.: Cold Spring Harbor Laboratory Press, p. 17.38 (1989); Ausubel, F. M., et al., in: *Current Protocols in Molecular Biology,* New York: John Wiley & Sons, pp. 4.4.1-4.4.7 (1993)). The permeabilization effects of these various chemical agents may be enhanced by concurrently treating the bacterial cells with detergents such as TRITON X-100®, sodium dodecylsulfate (SDS) or Brij 35 (Laurent, S. J., and Vannier, F. S., *Biochimie* 59:747-750 (1977); Felix, H., *Anal. Biochem.* 120:211-234 (1982); Hettwer, D., and Wang, H., *Biotechnol. Bioeng.* 33:886-895 (1989); Cull, M., and McHenry, C. S., *Meth. Enzymol.* 182:147-153 (1990); Schupp, J. M., et al., *BioTechniques* 19:18-20 (1995)), or with proteins or protamines such as bovine serum albumin or spermidine (McHenry, C. H., and Kornberg, A, *J. Biol. Chem.* 252(18):6478-6484 (1977); Felix, H., *Anal. Biochem.* 120: 211-234 (1982); Hughes, A. J., Jr., et al., *J. Cell. Biochem. Suppl.* 0 16 (Part B):84 (1992)).

In addition to these various chemical treatments, a number of physical methods of disruption have been used. These physical methods include osmotic shock, e.g., suspension of the cells in a hypotonic solution in the presence or absence of emulsifiers (Roberts, J. D., and Lieberman, M. W., *Biochemistry* 18:4499-4505 (1979); Felix, H., *Anal. Biochem.* 120: 211-234 (1982)), drying (Mowshowitz, D. B., *Anal. Biochem.* 70:94-99 (1976)), bead agitation such as ball milling (Felix, H., *Anal. Biochem.* 120:211-234 (1982); Cull, M., and McHenry, C. S., *Meth. Enzymol.* 182:147-153 (1990)), temperature shock, e.g., freeze-thaw cycling (Lazzarini, R. A., and Johnson, L. D., *Nature New Biol.* 243:17-20 (1975); Felix, H., *Anal. Biochem.* 120:211-234 (1982)), sonication (Amos, H., et al., *J. Bacteriol.* 94:232-240 (1967); Ausubel, F. M., et al., in: *Current Protocols in Molecular Biology,* New York: John Wiley & Sons, pp. 4.4.1-4.4.7 (1993)) and pressure disruption, e.g., use of a french pressure cell (Ausubel, F. M., et al., in: *Current Protocols in Molecular Biology,* New York: John Wiley & Sons, pp. 16.8.6-16.8.8 (1993)). Other approaches combine these chemical and physical methods of disruption, such as lysozyme treatment followed by sonication or pressure treatment, to maximize cell disruption and protein release (Ausubel, F. M., et al., in: *Current Protocols in Molecular Biology,* New York: John Wiley & Sons, pp. 4.4.1-4.4.7 (1993)).

These disruption approaches have several advantages, including their ability to rapidly and completely (in the case of physical methods) disrupt the bacterial cell such that the release of intracellular proteins is maximized. In fact, these approaches have been used in the initial steps of processes for the purification of a variety of bacterial cytosolic enzymes, including natural and recombinant proteins from mesophilic organisms such as *Escherichia coli, Bacillus subtilis* and *Staphylococcus aureus* (Laurent, S. J., and Vannier, F. S., *Biochimie* 59:747-750 (1977); Cull, M., and McHenry, C. S., *Meth. Enzymol.* 182:147-153 (1990); Hughes, A. J., Jr., et al., *J. Cell. Biochem. Suppl.* 0 16 (*Part B*):84 (1992); Ausubel, F. M., et al., in: *Current Protocols in Molecular Biology,* New York: John Wiley & Sons, pp. 4.4.1-4.4.7 (1993)), as well as phosphatases, restriction enzymes, DNA or RNA polymerases and other proteins from thermophilic bacteria and archaea such as *Thermus aquaticus, Thermus thermophilus, Thermus flavis, Thermus caldophilus, Thermotoga maritima,* and *Sulfolobus acidocaldarius* (Shinomiya, T., et al., *J. Biochem.* 92(6):1823-1832 (1982); Elie, C., et al., *Biochim. Biophys. Acta* 951(2-3):261-267 (1988); Palm, P., et al., *Nucl. Acids Res.* 21(21):4904-4908 (1993); Park, J. H., et al., *Eur. J. Biochem.* 214(1):135-140 (1993); Harrell, R. A., and Hand, R. P., *PCR Meth. Appl.* 3(6):372-375 (1994); Meyer, W., et al., *Arch. Biochem. Biophys.* 319(1):149-156 (1995)).

However, these methods possess distinct disadvantages as well. For example, the physical methods by definition involve shearing and fracturing of the bacterial cell walls and plasma membranes. These processes thus result in extracts containing large amounts of particulate matter, such as membrane or cell wall fragments, which must be removed from the extracts, typically by centrifugation, prior to purification of the enzymes. This need for centrifugation limits the batch size capable of being processed in a single preparation to that of available centrifuge space; thus, large production-scale preparations are impracticable if not impossible. Furthermore, physical methods, and many chemical permeation techniques, typically result in the release from the cells not only of the desired intracellular proteins, but also of undesired nucleic acids and membrane lipids (the latter particularly resulting when organic solvents are used to permeabilize the cells). These undesirable cellular components also complicate the subsequent processes for purification of the desired proteins, as they increase the viscosity of the extracts (Sambrook, J., et al., in: *Molecular Cloning: A Laboratory Manual,* 2nd ed., Cold Spring Harbor, N.Y.: Cold Spring Harbor Laboratory Press, p. 17.38 (1989); Cull, M., and McHenry, C. S., *Meth. Enzymol.* 182:147-153 (1990)), and bind with high avidity and affinity to nucleic acid-binding proteins such as DNA polymerases, RNA polymerases and restriction enzymes.

These limitations have been partially overcome in the case of proteins prepared from mesophilic bacteria. For example, mild chemical disruption of *E. coli, B. subtilis* and *Salmonella typhimurium* has been conducted to permeabilize these cells, allowing free mobility of proteins across the membrane of the cells or resultant spheroplasts, but inducing retention of most of the nucleic acids within the cell or spheroplast (Laurent, S. J., and Vannier, F. S., *Biochimie* 59:747-750 (1977); Hettwer, D., and Wang, H., *Biotechnol. Bioeng.* 33:886-895 (1989); Cull, M., and McHenry, C. S., *Meth. Enzymol.* 182:147-153 (1990); Schupp, J. M., et al., *BioTechniques* 19:18-20 (1995)). Similar approaches have also been taken to limit the contamination of protein preparations from thermophilic bacteria, based on the demonstration that protein-permeable spheroplast can be prepared from thermophiles like *Thermus thermophilus* by treatment with lysozyme with or without a detergent (Oshima, T., and Imahori, K., *Int. J. Syst. Bacteriol.* 24(1): 102-112 (1974)).

These approaches, however, are insufficient for preventing the contamination of preparations of thermostable enzymes with DNA. For example, it has been reported by at least two different groups that commercially available preparations of Taq DNA polymerase are contaminated with bacterial DNA (Rand, K. H., and Houck, H., *Mol. Cell Probes* 4(6):445-450 (1990); Hughes, M. S., et al., *J. Clin. Microbiol.* 32(8):2007-2008 (1994)), despite the use of gentle lysis procedures to liberate the enzyme from the cells. Furthermore, this contaminating DNA may come not only from the organisms which are the source of the enzyme (*Thermus aquaticus* for natural Taq polymerase; *E. coli* for recombinant enzyme), but also from unknown organisms present in the reagents and materials used to purify the enzyme after its release from the cells (Rand, K. H., and Houck, H., *Mol. Cell Probes* 4(6):445-450 (1990); Hughes, M. S., et al., *J. Clin. Microbiol.* 32(8): 2007-2008 (1994)). Since thermophilic enzymes such as DNA polymerases and restriction enzymes are routinely used in automated techniques of DNA amplification and sequencing, e.g., the Polymerase Chain Reaction (PCR), the presence of contaminating DNA in the enzyme preparations is a significant problem since it can give rise to spurious amplification or sequencing results. Thus, a need exists for preparations of thermostable enzymes that are substantially free of contamination by nucleic acids.

Various solutions to this problem have been suggested. For example, many investigators routinely run "no-template controls" to allow subtraction of any spurious results from their experimental samples, or to determine the extent of contamination of their enzyme preparations ((Rand, K. H., and Houck, H., *Mol. Cell Probes* 4(6):445-450 (1990)). This approach, however, increases the resource and time requirements, and thus the expense, of the assays, particularly in high-throughput settings such as in clinical applications of PCR. Also suggested have been methods of eliminating nucleic acids in the enzyme preparations, such as treatment of the preparations with DNAse or RNAse, restriction enzyme digestion, organic phase partitioning, or cesium chloride density gradient centrifugation (Cull, M., and McHenry, C. S., *Meth. Enzymol.* 182:147-153 (1990); Rand, K. H., and Houck, H., *Mol. Cell Probes* 4(6):445-450 (1990)), although these approaches have apparently not proved routinely successful at removing contaminating DNA (Rand, K. H., and Houck, H., *Mol. Cell Probes* 4(6);445-450 (1990)). Other methods of inactivating DNA have been described, such as a method of heating samples at 60-100° C. in the presence of an acid at pH 3-4 (U.S. Pat. No. 5,417,862). However, while thermophilic enzymes are fairly resistant to these increased temperatures, they quickly lose enzymatic activity when exposed to a pH below about 5, thus precluding use of this method in purging thermophilic enzyme preparations of nucleic acid contamination.

Thus, instead of attempting to remove nucleic acids from preparations of thermostable enzymes, a more reasonable and successful approach would be to prevent contamination of the enzymes by nucleic acids from the outset in the purification process. Such an approach would be two-pronged: 1) preventing release of nucleic acids from the bacterial cells during permeabilization of the cells to release the enzymes; and 2) preventing contamination of the enzymes during the purification process itself. Furthermore, an optimal method would obviate the need for centrifugation in the process, thus allowing large-scale, and even continuous, production of nucleic acid-free thermophilic enzymes. The present invention provides such methods, and thermophilic enzymes produced by these methods.

SUMMARY OF THE INVENTION

The present invention provides methods of making a thermostable enzyme which is substantially free of nucleic acids, comprising permeabilizing bacterial cells to form spheroplasts and isolating the thermostable enzyme under conditions S favoring the partitioning of nucleic acids from the thermostable enzyme. The invention is particularly directed to methods wherein the permeabilization of the bacterial cells is accomplished by contacting the cells with an aqueous solution comprising: a chaeotropic agent, preferably a guanidine salt and most preferably guanidine hydrochloride; and a non-ionic detergent, preferably TRITON X-100 or NP-40. The invention is further directed to such methods wherein the conditions favoring the partitioning of nucleic acids from the thermostable enzyme comprise formation of an ultrafiltrate by microfiltration of the spheroplasts through a semi-permeable membrane, which is preferably a hydrophilic dialysis membrane, in the presence of a salt, preferably ammonium sulfate or potassium chloride, and purification of the thermostable enzyme from the ultrafiltrate, preferably by chromatography using sterile materials. The invention is particularly directed to such methods wherein the bacterial cells providing the thermostable enzyme is a species of the genus *Thermus,* most preferably *Thermus aquaticus,* or a species of the genus *Thermotoga,* most preferably *Thermotoga neapolitana* or *Thermotoga maritima.* The invention is also directed to methods wherein the thermostable enzyme being prepared is a thermostable DNA polymerase, most preferably Taq DNA polymerase, Tne DNA polymerase, Tma DNA polymerase, or a mutant, derivative or fragment thereof, or a thermostable restriction endonuclease. The invention also provides the above-described enzymes, or mutants, derivatives or fragments thereof that are made according to the methods provided. The invention is also directed to methods for amplifying or sequencing a nucleic acid molecule comprising contacting said nucleic acid molecule with a thermostable DNA polymerase made according to the methods provided by the present invention. The invention also provides kits for amplifying or sequencing a nucleic acid molecule comprising a carrier means having in close confinement therein one or more container means, wherein a first such container means contains a thermostable enzyme, preferably a DNA polymerase or a restriction endonuclease, and most preferably Taq DNA polymerase, Tne DNA polymerase, Tma DNA polymerase, or a mutant, derivative or fragment thereof, made according to the methods of the present invention.

Other features and advantages of the present invention will be apparent to those skilled in the art from the following description of the preferred embodiments thereof, and from the claims

DETAILED DESCRIPTION OF THE INVENTION

Overview

The present invention provides thermostable enzymes, such as DNA polymerases and restriction endonucleases, that are substantially free from contamination with nucleic acids. As used herein, the term "substantially free of nucleic acids" means an enzyme composition that comprises no nucleic acids, or that comprises nucleic acids below the level of detection, when assayed by standard biochemical assays for nucleic acids, which may include gel electrophoresis (e.g., agarose gel electrophoresis coupled with ethidium bromide, acridine orange or Hoechst staining), spectrophotometry (e.g., ultraviolet, atomic absorption, NMR or mass spectrometry), chromatography (liquid, gas, HPLC or FPLC), or by functional assays for nucleic acids such as a measure of incorporation of $^3$H-labeled nucleotides by the enzyme preparation in a "no-template" nucleic acid amplification control. These biochemical and functional assays are described in more detail below, and in Example 3. The invention also provides methods for the production of these enzymes, and compositions and kits comprising these enzymes which may be used in amplifying or sequencing nucleic acid molecules, including through use of the polymerase chain reaction (PCR).

Briefly summarized, the present invention utilizes a scheme comprising permeabilization of bacterial cells to form spheroplasts, microfiltration of the spheroplasts to form a microfiltrate, ultrafiltration of the microfiltrate to form an ultrafiltrate, and purification of the enzyme from the ultrafiltrate, preferably by conventional liquid chromatography. The present invention 1) provides a method of large-scale (>20 million unity production of thermostable enzymes, including Taq DNA polymerase, which are substantially free of DNA contamination; and 2) provides a scalable method for the production of any desirable quantity of a thermostable enzyme.

The present methods are based in particular upon an optimized method of chemical permeabilization of bacterial cells, which strips the bacterial cell wall and yields spheroplasts, and an optimized method of microfiltration of the spheroplasts under conditions favoring the release of thermostable enzymes, but inhibiting the release of nucleic acids, from the spheroplasts. The permeabilization process has been optimized to allow intracellular enzymes, including DNA polymerase and restriction enzymes, to permeate the spheroplast membrane while preventing the cellular DNA from entering the permeation buffer. This approach provides an initial extract that is enriched in enzyme and that is relatively free of nucleic acids. The extract is then subjected to microfiltration under conditions (including precise definition of the variables of salt, pH, and choice of membrane chemistry) favoring release of the enzyme from the spheroplasts while preventing cells, cell debris and/or nucleic acids from crossing the filtration membrane barriers. Following microfiltration and ultrafiltration, thermostable enzymes may be purified by standard techniques such as chromatography or electrophoresis, to provide enzyme preparations which are substantially free from contamination by nucleic acids.

Bacterial Cell Sources of Thermostable Enzymes

Thermostable enzymes (e.g., DNA polymerases or restriction enzymes) may be prepared according to the methods of the present invention from a variety of thermophilic bacteria that are available commercially (for example, from American Type Culture Collection, Rockville, Md.). Suitable for use as sources of thermostable enzymes are the thermophilic bacteria *Thermus aquaticus, Thermus thermophilus, Thermococcus litoralis, Pyrococcus furiosus, Pyrococcus woosii* and other species of the *Pyrococcus* genus, *Bacillus stearothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants of each of these species. It will be understood by one of ordinary skill in the art, however, that any thermophilic microorganism may be used as a source for preparation of thermostable enzymes according to the methods of the present invention. Bacterial cells may be grown according to standard microbiological techniques, using culture media and incubation conditions suitable for growing active cultures of the particular species that are well-known to one of ordinary skill in the art (see, e.g., Brock, T. D., and Freeze, H., *J. Bacteriol.* 98(1):289-297 (1969); Oshima, T., and Imahori, K, *Int. J. Syst. Bacteriol.* 24(1):102-112 (1974)).

Permeabilization of Bacterial Cells

In the initial steps of the present methods, the bacterial cells which serve as the source for the thermostable enzymes are treated so as to permeabilize the cells by stripping away the cell walls and converting the cells into spheroplasts. Although a variety of techniques may be used for this permeabilization, such as treatment with enzymes (e.g., lysozyme), the production of substantially nucleic acid-free enzymes by the present invention requires the use of a permeabilization method which will produce spheroplasts that retain DNA within the spheroplast while allowing free permeation of intracellular proteins (including enzymes) across the spheroplast membrane. All procedures from permeabilization to final purification of the enzymes should be carried out at temperatures below normal room temperature, preferably at about 4-15° C., most preferably at about 4-10° C., to prevent enzyme denaturation and loss of activity. Furthermore, all materials used throughout the present methods (i.e., reagents, salts, chromatography resins, equipment) should be sterilized by heat or barrier sterilization techniques (as appropriate to the material to be sterilized), to prevent the contamination of the thermostable enzymes with nucleic acids.

This permeabilization is preferably accomplished by suspension of the bacterial cells in an aqueous solution comprising at least one chaeotropic agent and at least one nonionic detergent. Chaeotropic agents preferable for use in the methods of the present invention include salts of guanidine or urea, most preferably guanidine hydrochloride. Any nonionic detergent may be used; most preferable are octylphenoxy-polyethoxyethanol nonionic surfactant (TRITON X-100®), Brij 35, Tween 20 and Nonidet P40 (NP-40®), although other nonionic surfactants and mixtures thereof, such as N-alkyl-glucosides, N-alkylmaltosides, glucamides, digitonin, deoxycholate, 3-[(3-cholamidopropyl)-dimethylammonio]-1-propane-sulfonate (CHAPS) or cetyltrimethylammonium-bromide (CTAB) may also be used in the present compositions. Reagents such as chaeotropes, detergents, buffer salts, etc., are available commercially, for example from Sigma Chemical Co. (St. Louis, Mo.).

For permeabilization, bacterial cells are suspended in a buffered salt solution containing the chaeotrope(s) and detergent(s). Preferably, the solution is an aqueous solution with a distilled, deionized water ($dH_2O$) base consisting of trishydroxymethylaminomethane (TRIS® base) at a concentration of about 25-500 mM, preferably about 50-250 mM, more preferably about 50-150 mM, and most preferably about 100 mM, at a pH of about 7.0-9.0, preferably about 7.5-9.0, more preferably about 8.0-8.5, and most preferably about 8.5 (pH at about 20-25° C.). The concentration of the chaeotrope (e.g., guanidine hydrochloride) in the solution is preferably about 300-1000 mM, more preferably about 500-750 mM, and most preferably about 600 mM, while the nonionic detergent concentration is preferably about 1-5% (vol/vol), more preferably about 1-2.5%, and most preferably about 1.8%. The permeabilization buffer solution may also comprise other components, such as protease inhibitors (e.g., phenylmethylsulfonylfluoride, added at a final concentration of about 0.5 mM), reducing agents (e.g., β-mercaptoethanol or most preferably dithiothreitol at a final concentration of about 1 mM), and chelating agents (e.g., disodium ethylenediaminetetraacetic acid ($Na_2EDTA$), most preferably at a concentration of about 1.5 mM); this buffer composition is referred to hereinafter as "permeabilization buffer." It will be understood by one of ordinary skill in the art, however, that other suitable buffer compositions may be substituted with equivalent effect in the permeabilization process, provided that the above-described concentrations of chaeotropes and detergents are used.

For permeabilization, bacterial cells are suspended in permeabilization buffer at a concentration of about 100-1000 g (wet weight) of cells per liter of solution, preferably about 250-1000 g/L, and most preferably about 500 g/L (cell density of about $1-5\times10^{10}$ cells/gram, preferably about $2-5\times10^{10}$ cells/gram, and most preferably about $2.5\times10^{10}$ cells/gram). The cell suspension is gently stirred, preferably via magnetic or impeller stirring, in such a way as to prevent shearing and rupture of the cells. After about 30-60 minutes, most preferably about 45 minutes, a protein-extracting salt is added to the suspension to enhance the permeation of the intracellular enzymes across the spheroplast membranes Although any salt may be used in the present invention (except salts of toxic metals such as cadmium or other heavy metals), preferred salts include sodium chloride, potassium acetate, sodium acetate, ammonium acetate, ammonium chloride, ammonium sulfate or potassium chloride, most preferably ammonium sulfate or potassium chloride. Salt is added to the suspension at a concentration of about 100-500 mM, preferably about 100-300 mM, and most preferably about 400 mM for salts with monoatomic cations (e.g., sodium chloride, potassium acetate, sodium acetate, ammonium acetate, ammonium chloride or potassium chloride) or about 200 mM for salts with diatomic cations (e.g., ammonium sulfate). Salt should be gradually added to the solution, to provide for optimal solubilization. Following addition of the salt, the solution is mixed for about an additional 30-60 minutes, most preferably about an additional 45 minutes, during which time the bacterial cells are converted into spheroplasts and the intracellular proteins, including thermostable enzymes, begin to permeate the spheroplast membrane while cellular nucleic acids are retained within the spheroplast.

Microfiltration, Concentration and Diafiltration

Following permeabilization of the bacterial cells, thermostable enzymes are collected by subjecting the spheroplasts to microfiltration to release the enzymes from the spheroplasts and remove particulate matter, concentration of the microfiltrate, and diafiltration. Unlike other methods described in the background of the invention, the present methods obviate the need for precipitation of nucleic acids and the use of centrifugation techniques; this elimination of centrifugation facilitates the rapid production of thermostable enzymes at any scale in a continuous or discontinuous fashion. The general methods of microfiltration, concentration and diafiltration are generally well-known to one of ordinary skill, and will result in the preparation of a nucleic acid-free enzyme ultrafiltrate suitable for purification and characterization of the enzymes.

Microfiltration is preferably carried out by collecting the spheroplast solution in permeabilization buffer (described above) and diafiltering the solution against a filtration buffer through a semi-permeable membrane, most preferably a hydrophilic dialysis, microfiltration or ultrafiltration membrane. The filtration buffer preferably is a $dH_2O$-based solution comprising: a) a buffer salt, preferably trishydroxymethylaminomethane (TRIS® base) at a concentration of about 25-500 mM, preferably about 50-250 mM, more preferably about 50-150 mM, and most preferably about 100 mM, at a pH of about 7.5-9.5, preferably about 8.0-9.3, more preferably about 8.0-9.0, and most preferably about 8.9 (pH at 4° C.); and b) the protein-extracting salt which was added to the permeabilization buffer, which is preferably ammonium sulfate or potassium chloride, at a concentration of about 100-500 mM, preferably about 100-300 mM, and most preferably about 200 mM The filtration buffer solution may also comprise other components, such as protease inhibitors (e.g., phenylmethylsulfonylfluoride, added at a final concentration of about 0.5 mM), reducing agents (e.g., β-mercaptoethanol or most preferably dithiothreitol at a final concentration of about 1 mM), and chelating agents (e.g., disodium ethylenediaminetetraacetic acid ($Na_2EDTA$), most preferably at a concentration of about 1.5 mM); this buffer composition is referred to hereinafter as "filtration buffer." It will be understood by one of ordinary skill in the art, however, that other suitable buffer compositions may be substituted with equivalent effect in the filtration process, provided that the above-described pH levels and concentration of protein-extracting salt are used.

Preferable for use in microfiltration is a system allowing permeation of intracellular enzymes through the membrane and into the filtrate, leaving spheroplasts (with the nucleic acids retained therein) and particulate matter in the retentate. One suitable system providing such conditions is, for example, a hollow fiber microfiltration system which is commercially available (Microgon), although similar systems providing the same results will be known to one of ordinary skill. Following microfiltration in this manner, the filtrate contains the thermostable enzymes which are substantially free of nucleic acids such as DNA, as the DNA is partitioned from the enzymes by being retained with the particulate matter. This filtrate may then be concentrated, for example by membrane concentration through a semi-permeable membrane using a commercially available system (Amicon) or equivalent. The enzymes may then be individually purified from the concentrate as described below; alternatively, the concentrate may be diafiltered as described above against a suitable buffer solution to place the enzymes into an appropriate chemical environment for purification, as described in more detail in Example 2.

Purification and Characterization of Enzymes

Following concentration or diafiltration as described above, thermostable enzymes may be purified by a variety of protein purification techniques that are well-known to one of ordinary skill in the art. Suitable techniques for purification include, but are not limited to, ammonium sulfate or ethanol precipitation, acid extraction, preparative gel electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography. Most preferably, the enzymes are purified by a combination of liquid chromatographic techniques including ion exchange, affinity and size exclusion methods such as those described in Example 3, although alternative chromatographic solid supports, mobile phases and associated methods may be equivalently used and will be well-known to one of ordinary skill. Since all materials and equipment used in the chromatographic purification of the enzymes are sterilized or prepared so as to eliminate bacterial contamination, the enzyme preparations of thermostable enzymes produced by this purification scheme will remain substantially free of nucleic acids such as DNA.

Assays for DNA Content

Purified thermostable enzymes made according to the present invention may be examined for nucleic acid content by a variety of methods which are well-known to one of ordinary skill in the art. For example, a sample of the final product can be assayed by ultraviolet spectrophotometry, comparing absorption of light by the sample at a wavelength of 260 nm ($A_{260}$, the absorption maximum for DNA) to that at 280 nm ($A_{280}$, the absorption maximum for tryptophan, which is found in most proteins); the lower the $A_{260}/A_{280}$ ratio, the lower the content of DNA in the sample. Samples with minimal $A_{260}/A_{280}$ values may then be pooled to constitute a substantially nucleic acid-free preparation of thermostable enzymes.

Alternatively, samples may be directly assayed for the presence of DNA by gel electrophoresis or dot blotting and staining with a DNA-binding dye (e.g., ethidium bromide, acridine orange, Hoechst stain) or antibody, which are commercially available, for example, from Sigma (St. Louis, Mo.). In addition, the DNA content of samples of DNA polymerases may be examined by carrying out an amplification reaction in the absence of exogenously added DNA template,. either as a "no-template control" in a standard PCR assay (Rand, K. H., and Houck, H., *Mol. Cell Probes* 4(6):445-450 (1990)), or by specifically designing an assay to measure DNA content by radiolabeled nucleotide incorporation into salmon testes or bovine thymus DNA, according to methods that are standard in the art. Use of such assays will allow one of ordinary skill, without undue experimentation, to identify samples of thermostable enzymes obtained by the purification schemes described above, which may then be pooled and used as preparations of substantially nucleic acid-free thermostable enzymes.

Formulation of Enzymes

Following their purification, the substantially DNA-free thermostable enzymes may be stored until use in a buffered solution at temperatures of about −80° to 25° C., most preferably at −80° to 4° C., or in lyophilized form. Alternatively, the enzymes may be stabilized by drying in the presence of a sugar such as trehalose (U.S. Pat. Nos. 5,098,893 and 4,824, 938) or acacia gum, pectin, carboxymethylcellulose, carboxymethylhydroxyethylcellulose, guar, carboxy guar, carboxymethylhydroxypropyl guar, laminaran, chitin, alginates or carrageenan. In addition, the enzymes provided by the present invention may be directly formulated into compositions to be used in techniques requiring the use of thermostable enzymes, such as compositions for nucleic acid sequencing or amplification in the case of thermostable DNA polymerases such as Taq, Tne, or Tma DNA polymerases, or mutants, derivatives or fragments thereof These formulations may be concentrated solutions of the enzymes, or solutions of the enzymes at working concentrations which may comprise additional components and which may be prepared as described in co-pending U.S. patent application Ser. No. 08/689,815, by Ayoub Rashtchian and Joseph Solus, entitled "Stable Compositions for Nucleic Acid Sequencing and Amplification," filed Aug. 14, 1996, which is incorporated by reference herein in its entirety.

Kits

In other preferred embodiments, the substantially DNA-free thermostable enzymes provided by the present invention may be assembled into kits for use in methods requiring thermostable enzymes, such as nucleic acid amplification or sequencing utilizing thermostable DNA polymerases such as Taq, Tne or Tma DNA polymerases or mutants, fragments or derivatives thereof. A DNA amplification kit according to the present invention comprises a carrier means having in close confinement therein one or more container means, such as vials, tubes, bottles and the like, wherein a first container means contains a substantially DNA-free thermostable enzyme, preferably a substantially DNA-free thermostable DNA polymerase or a thermostable restriction enzyme, and most preferably a substantially DNA-free preparation of Taq DNA polymerase, Tne DNA polymerase, Tma DNA polymerase, or a mutant, derivative or fragment thereof. The amplification kit encompassed by this aspect of the present invention may further comprise additional reagents and compounds necessary for carrying out standard nucleic amplification protocols (See U.S. Pat. Nos. 4,683,195 and 4,683,202, which are directed to methods of DNA amplification by PCR).

Similarly, a DNA sequencing kit according to the present invention comprises a carrier means having in close confinement therein one or more container means, such as vials, tubes, bottles and the like, wherein a first container means contains a substantially DNA-free thermostable enzyme, preferably a substantially DNA-free thermostable DNA polymerase or a thermostable restriction enzyme, and most preferably a substantially DNA-free preparation of Taq DNA polymerase, Tne DNA polymerase, Tma DNA polymerase, or a mutant, derivative or fragment thereof The sequencing kit may further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing).

Use of the Substantially DNA-free Thermostable Enzymes

The substantially DNA-free thermostable enzymes and kits embodied in the present invention will have general utility in any application utilizing thermostable enzymes, including but not limited to nucleic acid amplification or sequencing methodologies. Amplification methods in which the present enzymes may be used include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). Nucleic acid sequencing techniques which may employ the present enzymes include dideoxy sequencing methods such as those disclosed in U.S. Pat. Nos. 4,962,022 and 5,498,523, as well as more complex PCR-based nucleic acid fingerprinting techniques such as Random Amplified Polymorphic DNA (RAPD) analysis (Williams, J. G. K., et al., *Nucl. Acids Res.* 18(22):6531-6535, 1990), Arbitrarily Primed PCR (AP-PCR; Welsh, J., and McClelland, M., *Nucl. Acids Res.* 18(24):7213-7218, 1990), DNA Amplification Fingerprinting (DAF; Caetano-Anollés et al, *Bio/Technology* 9:553-557, 1991), microsatellite PCR or Directed Amplification of Minisatellite-region DNA. (DAMD; Heath, D. D., et al., *Nucl. Acids Res.* 23(24): 5782-5785, 1993), and Amplification Fragment Length Polymorphism (AFLP) analysis (EP 0 534 858; Vos, P., et al., *Nucl. Acids Res.* 23(21):4407-4414, 1995; Lin, J. J., and Kuo, J., *FOCUS* 17(2):66-70, 1995). In particular, the enzymes and kits of the present invention will be useful in the fields of medical therapeutics and diagnostics, forensics, and agricultural and other biological sciences, in any procedure utilizing thermostable enzymes such as thermostable DNA polymerases or thermostable restriction endonucleases.

It will be readily apparent to those skilled in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Example 1

Permeabilization of Bacterial Cells

In the initial steps of the purification process, bacterial cells (*Thermus aquaticus*, strain YT-1), which were obtained directly from actively growing cultures, or which were stored at −20° C. and partially thawed, were suspended at 500 g of cells/L into cold (4° C.) of permeabilization buffer (100 mM TRIS, 1.8% TRITON X-100, 600 mM guanidine HCl, 1.5 mM EDTA, 1 mM dithiothreitol (DTT), pH 8.5). During suspension of the cells in the buffer, phenylmethylsulfonylfluoride (PMSF) was added to a final concentration of 0.5 mM. Cells were stirred for about 45 minutes at 4° C. to ensure complete suspension, and then ammonium sulfate was added to a final concentration of 200 mM and the cell suspension was stirred for an additional 45 minutes. During this time, cells were permeabilized via the action of the guanidine HCl and TRITON X-100, and intracellular protein release into the buffer was enhanced by the action of the ammonium sulfate.

Example 2

Microfiltration, Concentration and Diafilitration of Extracts

Following permeabilization, one volume of filtration buffer (100 mM TRIS, 200 mM ammonium sulfate, 1 mM EDTA, 1 mM DTT, pH 8.9) was added to the cell suspension, and the suspension mixed completely. Microfiltration of the suspension was then carried out through a 0.2 µm Microgon mixed ester cellulose hollow fiber system, using a recirculation rate of 90 L/min. The suspension was diafiltered with six volumes of cold filtration buffer, collecting the permeate in a suitable sized chilled (4° C.) container. Under these conditions, thermostable enzymes passed through the membrane with the permeate, leaving the bacterial cells with most of the DNA in the retentate.

As the ultrafiltration proceeded, concentration of the permeate was begun once a sufficient volume had been collected to prime the second ultrafiltration system. Permeate was concentrated using an Amicon DC-90 system, through Nicrogon 10,000 MWCO membrane (although alternative membrane systems of 10,000 MWCO, such as a Filtron system, a Millipore plate and frame system, or membrane from AG Technologies, may be used equivalently) and an in-line chiller to minimize heat build-up from the pumping system. Permeate was concentrated to approximately the original volume of the extract (see Example 1), and was then diafiltered against about seven volumes of diafiltration buffer (25 mM Bicine, 10 mM KCl, 1 mM EDTA, 1 mM DTT, pH 8.9), until the conductivity was $\leq$3 mS. Ultrafiltrate was then immediately used for purification of enzyme (Example 3), or was stored at −80° to 4° C. until use. For storage, ultrafiltrate is most preferably lyophilized and stored at −20° C., although ultrafiltrate solution may alternatively be formulated into 50% (w/v) glycerol and stored at −20° C. or pre-loaded onto Fractogel $SO_3$ matrix (see Example 3A below) and stored at 4° C. until use.

Example 3

Purification and Characterization of DNA-free Taq DNA Polymerase

Purification of enzyme from ultrafiltrate was accomplished by a series of chromatographic steps, using a procedure modified slightly from that described for purification of T5 DNA polymerase from *E. coli* (Hughes, A. J., Jr., et al., *J. Cell. Biochem. Suppl.* 0 16 (*Part B*):84 (1992)).

A. Fractogel $SO_2$

In the first chromatographic step, ultrafiltrate was passed over a Fractogel EMD $SO_3^-$-650(M) column (EM Separation Technologies, which removes most of the Taq I restriction enzyme and crude proteins from the ultrafiltrate. Ultrafiltrate was passed through a polypropylene depth filter to remove any residual precipitation, and loaded onto the Fractogel column at a flow rate of about 30 cm/hr. The column was then washed with 10 volumes of diafiltration buffer, and a 20 volume gradient from diafiltration buffer to $SO_3$ elution buffer (25 mM bicine, 500 mM KCl, 1 mM EDTA, 1 mM DTT, pH 8.9) run at a flow rate of about 30 cm/hr. Fractions were then collected for assay in diafiltration buffer for Taq DNA polymerase activity, starting with those fractions corresponding to the major UV peak. Assays were performed as described below under section F entitled "Cross-column Assays." Fractions demonstrating at least ½ of peak polymerase activity were pooled and subjected to further purification B. Single-Stranded DNA Agarose Column Pooled eluate from the Fractogel column was concentrated using a Pellicon 5 ft$^2$ apparatus, 10,000 MWCO with a T-screen Filtron cassette and a flow rate of 3 L/min at 10 psi until the volume was about ½ the starting volume. The sample was then diafiltered with low salt SS DNA agarose buffer (25 mM $K_2PO_4$, 10 mM KCl, 1 mM EDTA, 10% (vol/vol) glycerol, 1 mM DTT, pH 6.5) until the conductivity of the retentate reached <3.5 mS at 4° C. Sample was applied to a SS DNA agarose column (LTI; Gaithersburg, Md.) at a flow-rate of 10 cm/hour, and the column was then washed with 10 volumes of low salt SS DNA agarose buffer at a flow-rate of 20 cm/hour Enzyme was then eluted with a 20 column volume gradient from low salt SS DNA agarose buffer to high salt SS DNA agarose buffer (750 mM KCl) at a flow rate of 10 cm/hr. Fractions were collected as described above for Taq DNA polymerase activity assay, and fractions showing at least ½ of peak activity were pooled (the enzyme usually elutes between 30 and 40% of the gradient) and subjected to further purification.

C. Ceramic Hydroxyapatite, type A

Sample from the SS DNA agarose column was applied to a ceramic hydroxyapatite column (AIC, Inc.), which removes residual endonucleases and other non-specific proteins, at a flow rate of 10 cm/hr. The column was then washed with 1-2 column volumes of low salt ceramic HTP buffer (20 mM $K_2PO_4$, 100 mM KCl, 10% glycerol, 1 mM DTT, pH 6.5), and the enzyme eluted with a 10 column volume linear gradient of low salt ceramic HTP buffer to high salt ceramic HTP buffer (500 mM $K_2PO_4$) at 10 cm/hr, and fractions collected, assayed and pooled as described above (the enzyme usually elutes as a major UV peak 35 to 45% through the gradient).

D. AF-Heparin-650M

Eluate from the ceramic hydroxyapatite column was then applied to an AF-Heparain-650M affinity column (Toso-Haas), which removes residual proteins and results in single-band purity Taq polymerase.

Pooled eluate from the ceramic hydroxyapatite column was diafiltered against five volumes of low salt AF-heparin buffer (25 mM K2PO4, 10 mM KCl, 1 mM EDTA, 1 mM DTT, pH 6.5) using a Filtron system with a T-screen, 10,000 MWCO omega membrane cassette until the conductivity level reached ≦5 mS at 4° C. If a precipitate appeared, sample was filtered thru a 0.4-5 µm low protein-binding membrane filter prior to loading onto the column. Sample was loaded onto the AF-Heparin column at a flow rate of 25 cm/hr, and the column then washed with 10 column volumes of low salt AF-heparin buffer at 25 cm/hr. Enzyme was then eluted with a 20 column volume gradient of low salt AF-heparin buffer to high salt AF-heparin buffer (750 mM KCl) at 25 cm/hr. Fractions were collected, assayed and pooled as described above (the enzyme typically eluted as a major UV peak ~40 to 45% of the gradient).

E. Dialysis

AF-Heparin pool was dialyzed against 12 volumes of dialysis buffer (20 mM TRIS, 0.1 mM EDTA, 50% (vol/vol) glycerol, 1 mM DTT, pH 8.0) for 5 hours, then dialyzed overnight against 12 volumes of fresh dialysis buffer. Following dialysis, an equal volume of dialysis buffer was added to the dialyzed pool, and the pool mixed by magnetic stirring for about 1 hour at 4° C. Purified enzyme bulk was then stored at −20° C. until use.

F. Across-column Assays:

To determine polymerase activity in fractions at each step of the purification process, an assay modified from that described previously (Lehman, I. R., et al., *J. Biol. Chem.* 233(1):163-170 (1958)) was used. Briefly, tubes containing a reaction mixture (30 µl each) were prepared, with each tube containing 5 µl of column fraction sample in 25 µl of assay buffer (25 mM TAPS (pH 9.3), 2 mM $MgCl_2$, 50 mM KCl, 1 mM DTT, 0.2 mM each of dATP, dTTP, dGTP and dCTP, 0.4 mCi/ml of [$^3$H]dTTP (40 Ci/mmol), and 500 µg/ml of activated salmon testes DNA). Samples were vortexed gently and incubated at 72° C. for 10 minutes. After incubation, tubes were placed on ice for five minutes, microcentrifuged for five seconds, and then a 20 µl sample from each tube was spotted onto a GF/C filter and washed with cold 10% (w/v) trichloroacetic acid (TCA)/1% (w/v) sodium pyrophosphate for five minutes, followed by three washes with 5% TCA for three minutes each, and two washes in absolute ethanol for three minutes each. The filters were then dried under a heat lamp for fifteen minutes and then placed into Econofluor and quantified for $^3$H in a Beckman scintillation counter.

G. DNA Contamination Assays:

To determine the extent of DNA contamination of various preparations of Taq DNA polymerase, samples of Taq DNA polymerase obtained from commercial sources were compared to a preparation made according to the methods of the present invention in a polymerase assay similar to that outlined above, except that no salmon testes DNA template was included in the reaction mixture. Briefly, reaction mixtures (500 µl) containing 25 mM TAPS (pH 9.3), 10 mM $MgCl_2$, 50 mM KCl, 1 mM DTT, 100 µM each of dATP, dTTP, dGTP and dCTP, and 600 cpm of [$^3$H]dTTP/pmol of total nucleotide, were prepared and preincubated at 72° C. for five minutes. 100 units of purified Taq DNA polymerase was added to initate the reaction and at the times indicated in FIGS. 1 and 2, a 30 µl sample was removed and added to a vial containing 5 µl of 500 mM EDTA on ice. Once all time points had been collected, a 20 µl aliquot of the quenched reaction sample was applied to a GF/C filter, which were washed, dried and counted as described above. Results were expressed as $^3$H incorporation (cpm) at each time point.

Figure 1:
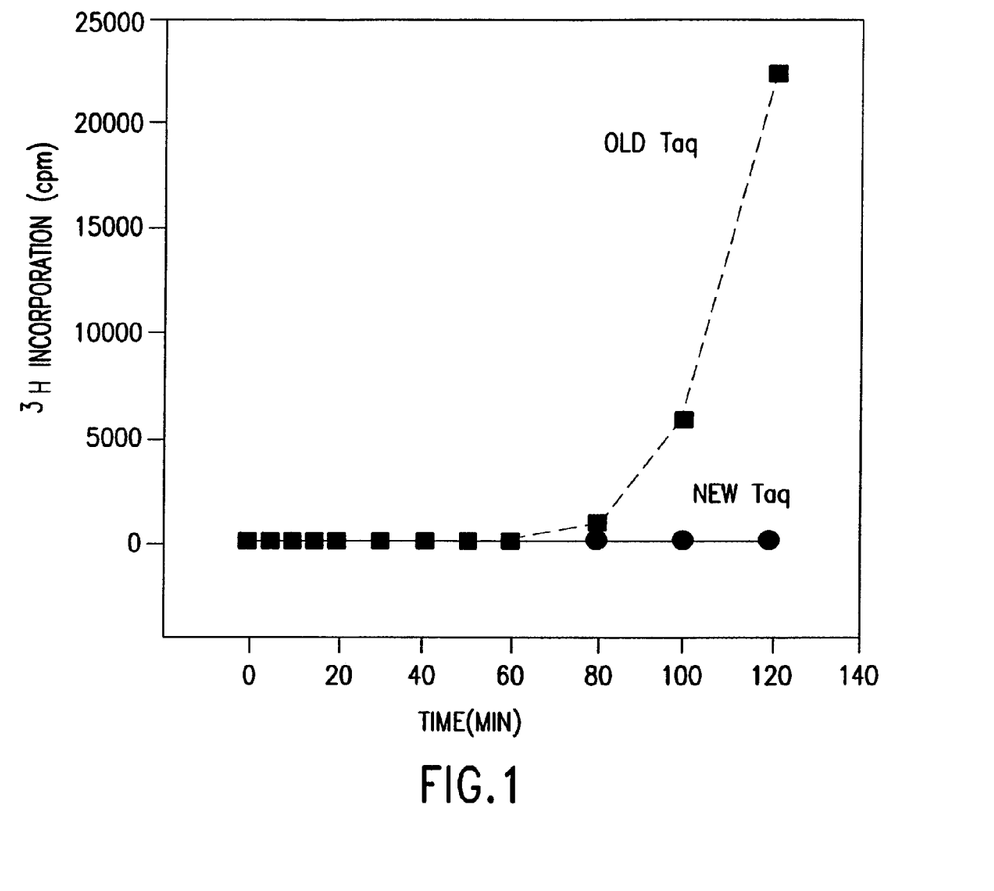
FIG. 1 is a graph of the incorporation of $^3$H-thymidine by two Taq DNA polymerase preparations in the absence of exogenously added template, demonstrating that a preparation of Taq DNA polymerase made according to the methods of the present invention ("New Taq") is substantially free from contamination with DNA, while a preparation of Taq DNA polymerase made according to standard methods ("Old Taq") contains significant amounts of DNA.

As shown in FIG. 1, a sample of purified Taq DNA polymerase (i.e., dialysed eluate from the AF-Heparin column above) prepared according to the methods of the present invention ("New Taq") demonstrated no detectable incorporation of [$^3$H]TTP over a period of incubation of 120 minutes. A commercial preparation of Taq polymerase made according to traditional methods ("Old Taq"), however, showed significant nucleotide incorporation beginning at 80 minutes of incubation, and increasing thereafter. These results indicate that preparations of Taq DNA polymerase provided by the present invention do not incorporate nucleotides in the absence of exogenously added template DNA, demonstrating that the present preparations of Taq DNA polymerase are substantially free from contamination with nucleic acids, while those obtained by traditional manufacturing methods contain significant amounts of contaminating DNA.

Figure 2:
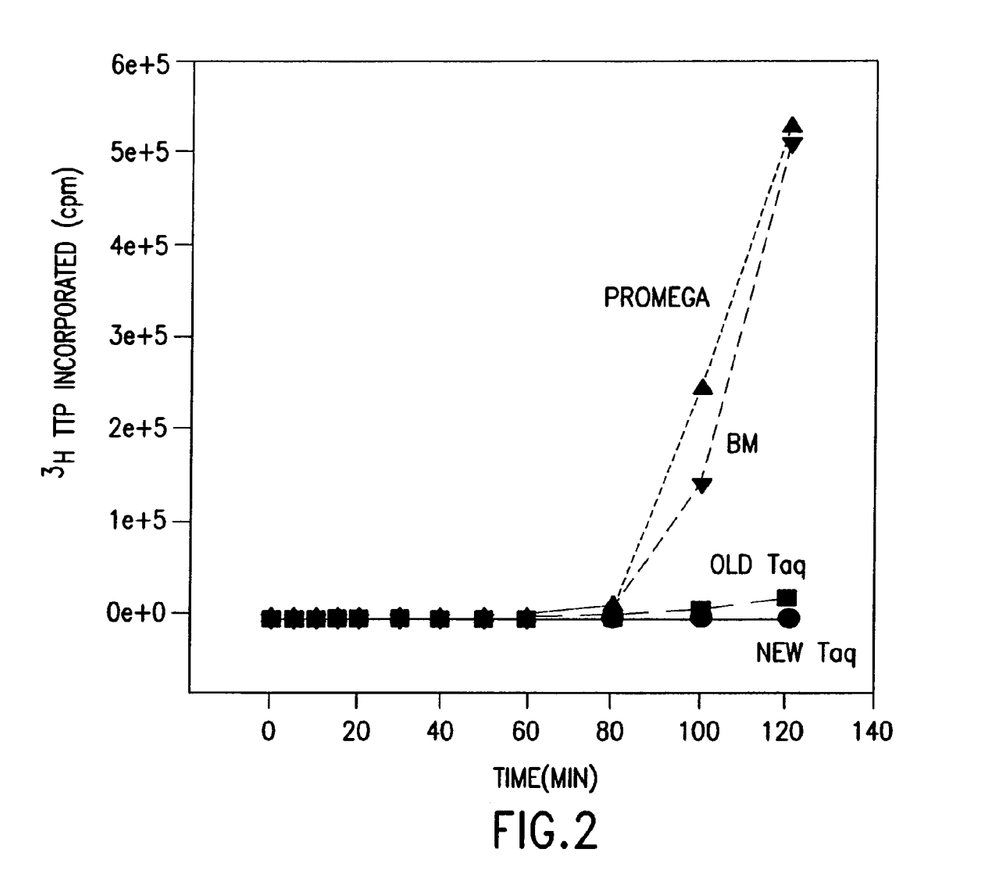
FIG. 2 is a graph of the incorporation of $^3$H-thymidine by various preparations of Taq DNA polymerase in the absence of exogenously added template, demonstrating that a preparation of Taq DNA polymerase made according to the methods of the present invention ("New Taq") is substantially free from contamination with DNA, while various commercially available preparations of Taq DNA polymerase contain significant amounts of DNA.

To confirm these results, other commercially available preparations of Taq DNA polymerase were compared to the preparations provided by the present invention for their DNA content. As shown in FIG. 2, commercial preparations of Taq DNA polymerase obtained from two other vendors ("Promega," "BM") contained substantial amounts of contaminating DNA, as indicated by the significant incorporation of [$^3$H]TTP in samples containing these preparations at reaction times greater than 80 minutes. As seen above, however, the present preparations of Taq DNA polymerase ("New Taq") demonstrated no detectable incorporation of [$^3$H]TTP over an incubation period of 120 minutes. Together, these results indicate that preparations of Taq DNA polymerase provided by the present invention are substantially free of nucleic acids, while several commonly used commercial preparations of Taq DNA polymerase contain substantial amounts of contaminating DNA.

Having now fully described the present invention it will be understood by those of ordinary skill in the art that the same can be performed within a wide and equivalent range of conditions, formulations and other parameters without affecting the scope of the invention or any embodiment thereof.

All publications, patents and patent applications cited herein are indicative of the level of skill of those skilled in the art to which this invention pertains, and are herein incorporated by reference in their entirety.

What is claimed is:

1. A nucleic acid synthesis method comprising contacting a sample nucleic acid with an aqueous and active thermostable DNA polymerase preparation that is substantially free of nucleic acids as determined by an assay comprising determining the A260/A280 ratio of said preparation by ultraviolet spectrophotometry; and synthesizing a nucleic acid complementary to said sample nucleic acid.

2. A nucleic acid synthesis method comprising contacting a sample nucleic acid with an aqueous and active thermostable DNA polymerase preparation that is substantially free of nucleic acids as determined by an assay comprising electrophoresis of said preparation on an electrophoretic gel and staining the gel with a DNA-binding dye or antibody; and synthesizing a nucleic acid complementary to said sample nucleic acid.

3. A nucleic acid synthesis method comprising contacting a sample nucleic acid with an aqueous and active thermostable DNA polymerase preparation that is substantially free of nucleic acids as determined by an assay comprising chromatographically measuring the amount of DNA in said preparation; and synthesizing a nucleic acid complementary to said sample nucleic acid.

4. A nucleic acid synthesis method comprising contacting a sample nucleic acid with an aqueous and active thermostable DNA polymerase preparation that is substantially free of nucleic acids as determined by measuring incorporation of a nucleotide in the absence of an exogenous nucleic acid template; and synthesizing a nucleic acid complementary to said sample nucleic acid.

5. The nucleic acid synthesis method of any of claims 1-4, wherein said DNA polymerase is Taq DNA polymerase, Tne DNA polymerase, Tma DNA polymerase, or a mutant, derivative or fragment thereof having DNA polymerase activity.

6. A nucleic acid amplification method comprising contacting a sample nucleic acid with an aqueous and active thermostable DNA polymerase preparation that is substantially free of nucleic acids as determined by an assay comprising determining the A260/A280 ratio of said preparation by ultraviolet spectrophotometry; and amplifying said sample nucleic acid.

7. A nucleic acid amplification method comprising contacting a sample nucleic acid with an aqueous and active thermostable DNA polymerase preparation that is substantially free of nucleic acids as determined by an assay comprising electrophoresis of said preparation on an electrophoretic gel and staining the gel with a DNA-binding dye or antibody; and amplifying said sample nucleic acid.

8. A nucleic acid amplification method comprising contacting a sample nucleic acid with an aqueous and active thermostable DNA polymerase preparation that is substantially free of nucleic acids as determined by an assay comprising chromatographically measuring the amount of DNA in said preparation; and amplifying said sample nucleic acid.

9. A nucleic acid amplification method comprising contacting a sample nucleic acid with an aqueous and active thermostable DNA polymerase preparation that is substantially free of nucleic acids as determined by measuring incorporation of a nucleotide in the absence of an exogenous nucleic acid template; and amplifying said sample nucleic acid.

10. The nucleic acid amplification method of any of claims 6-9, wherein said DNA polymerase is Taq DNA polymerase, Tne DNA polymerase, Tma DNA polymerase, or a mutant, derivative or fragment thereof having DNA polymerase activity.

11. A nucleic acid sequencing method comprising contacting a sample nucleic acid with an aqueous and active thermostable DNA polymerase preparation that is substantially free of nucleic acids as determined by an assay comprising determining the A260/A280 ratio of said preparation by ultraviolet spectrophotometry; and determining sequence of said sample nucleic acid.

12. A nucleic acid sequencing method comprising contacting a sample nucleic acid with an aqueous and active thermostable DNA polymerase preparation that is substantially free of nucleic acids as determined by an assay comprising electrophoresis of said preparation on an electrophoretic gel and staining the gel with a DNA-binding dye or antibody; and determining sequence of said sample nucleic acid.

13. A nucleic acid sequencing method comprising contacting a sample nucleic acid with an aqueous and active thermostable DNA polymerase preparation that is substantially free of nucleic acids as determined by an assay comprising chromatographically measuring the amount of DNA in said preparation; and determining sequence of said sample nucleic acid.

14. A nucleic acid sequencing method comprising contacting a sample nucleic acid with an aqueous and active thermostable DNA polymerase preparation that is substantially free of nucleic acids as determined by measuring incorporation of a nucleotide in the absence of an exogenous nucleic acid template; and determining sequence of said sample nucleic acid.

15. The nucleic acid sequencing method of any of claims 11-14, wherein said DNA polymerase is Taq DNA polymerase, Tne DNA polymerase, Tma DNA polymerase, or a mutant, derivative or fragment thereof having DNA polymerase activity.

16. The nucleic acid synthesis method of claim 4, wherein said nucleotide is 3H-labeled.

17. The nucleic acid amplification method of claim 9, wherein said nucleotide is 3H-labeled.

18. The nucleic acid sequencing method of claim 14, wherein said nucleotide is 3H-labeled.

* * * * *